United States Patent [19]

Demus et al.

[11] Patent Number: 4,585,576
[45] Date of Patent: Apr. 29, 1986

[54] LIQUID-CRYSTAL NEMATIC SUBSTANCES

[75] Inventors: Dietrich Demus; Horst Zaschke, both of Halle; Sabine Richter, Haldensleben; Hans-Joachim Deutscher; Adelbert Wiegeleben, both of Halle, all of German Democratic Rep.

[73] Assignee: VEB Werk für Fernsehelektronik im VEB Kombinat Mikroelektronik, Berlin, German Democratic Rep.

[21] Appl. No.: 602,832

[22] Filed: Apr. 23, 1984

[51] Int. Cl.⁴ ............ C09K 3/34; C07C 69/74; C07C 61/29; C07C 121/00; G02F 1/13

[52] U.S. Cl. .................. 252/299.62; 252/299.5; 558/414; 558/406; 558/401; 350/350 R; 560/5; 560/102; 560/116; 560/117; 562/403

[58] Field of Search ............ 252/299.5, 299.62; 350/350 R; 260/465 D, 465 H; 560/5, 102, 116, 117; 562/403

[56] References Cited

U.S. PATENT DOCUMENTS

| | | | |
|---|---|---|---|
| 3,984,419 | 10/1976 | Hauck et al. | 560/103 |
| 4,386,007 | 5/1983 | Krause et al. | 252/299.5 |
| 4,421,670 | 12/1983 | Deutscher et al. | 252/299.62 |
| 4,432,885 | 2/1984 | Petrzilka et al. | 252/299.62 |
| 4,434,073 | 2/1984 | Sucrow et al. | 252/299.62 |
| 4,438,268 | 3/1984 | Zaschke et al. | 252/299.62 |

FOREIGN PATENT DOCUMENTS

| | | | |
|---|---|---|---|
| 210920 | 6/1984 | German Democratic Rep. | 252/299.62 |
| 210899 | 6/1984 | German Democratic Rep. | 252/299.62 |
| 56-46855 | 4/1981 | Japan | 252/299.62 |
| 56-108740 | 8/1981 | Japan | 252/299.62 |
| 57-159753 | 10/1982 | Japan | 252/299.62 |
| 2082179 | 3/1982 | United Kingdom | 252/299.62 |
| 2116197 | 9/1983 | United Kingdom | 252/299.62 |

*Primary Examiner*—Teddy S. Gron
*Attorney, Agent, or Firm*—Jordan and Hamburg

[57] ABSTRACT

What is described is an improved opto-electronic component and display which uses novel liquid crystal nematic substances for the control of the light transmission and for the display of numbers symbols and images. The novel nematic liquid crystal substances herein, which exhibit high clearing temperatures, low working temperatures and rapid switching times, are 7-alkyl-perhydrophenanthren-2-carboxylic acids and esters thereof.

15 Claims, No Drawings

LIQUID-CRYSTAL NEMATIC SUBSTANCES

BACKGROUND OF THE INVENTION

The invention relates to opto-electronic components, and, more particularly, to liquid crystal nematic substances for the control of the light transmission and for the display of figures, symbols and images. Furthermore it relates to liquid crystal 7-alkyl-perhydrophenanthren-2-carboxylic acids and esters, and to the method of making such compounds.

A very large number of chemical compounds are known to have liquid crystal nematic characteristics D. Demus. H. Demus and H. Zaschke, Fluessige Kristalle in Tabellen, VEB Deutscher Verlag fuer Grundstoffindustrie, 2. Auflage Leipzig 1976. None of these individual compounds, however have the required properties which are necessary for optimum use of the compounds as liquid crystals in opto-electronic components. For this reason, mixtures of several such liquid crystal compounds have been heretofore used in opto-electronic components.

The temperature ranges under which such mixtures can be used in commercial application are of particular importance. For example, clearing temperatures of 70° and above, and working temperatures of −10° C. and below are particularly desired. In addition, the cell switching times should not be excessively high at low temperatures.

Accordingly, it is an object of the present invention to provide novel nematic liquid crystal compounds which have operable temperature ranges indicating high clearing temperatures, low working temperatures and favorable switching times.

Another object of the invention is to provide new nematic liquid crystal 7-alkyl-perhydrophenanthren-2-carboxylic acids and esters thereof, compositions thereof, and a method for such production of the compounds.

Still another object of the invention is to provide an opto-electronic display which uses as a cell component a novel liquid crystal nematic 7-alkyl-perhydrophenanthren-2-carboxylic acid or ester compound as a nematic liquid crystal substance.

SUMMARY OF THE INVENTION

In accordance with the foregoing objects, there is provided herein nematic liquid-crystal substances for use in opto-electronic components which substances have high transition temperatures, low working temperatures and rapid switching times. These substances are novel liquid-crystal 7-alkyl-perhydrophenanthren-2-carboxylic acids and esters which may be used individually, as mixtures with each other, or in combination with other liquid-crystal compounds.

The novel 7-alkyl-perhydrophenanthren-2-carboxylic acid esters have the general formula

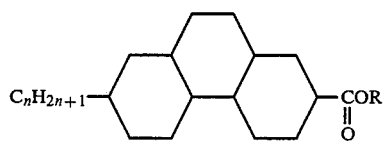

wherein R is

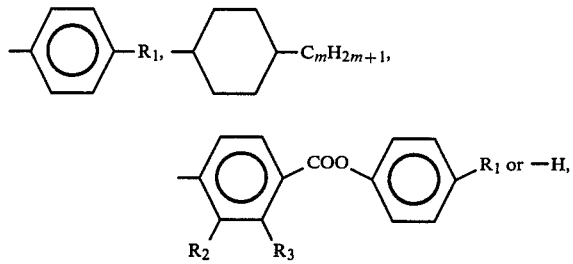

and wherein $R_1$ is $-C_mH_{2m+1}$, $-OC_mH_{2m+1}$, $-CH=C(CN)_2$, $-CN$, $-C_2H_4-CN$, $-NO_2$, $-F$, $-Cl$, $-Br$, or $-I$, and $R_2$ and $R_3$ are individually selected from $-H$, $-CH_3$, $-F$, $-Cl$ and $-CN$, and n and m are 1 to 14.

DETAILED DESCRIPTION OF PREFERRED EMBODIMENTS

In accordance with the synthesis feature of the invention, the novel acids are produced in high purity and good yield by complete hydrogenation of 7-alkyl-9,10-dihydrophenanthren-2-carbon acids at high pressure (10–13 atm) in aqueous base, e.t. potassium hydroxide at temperatures of 200° to 270° C. in the presence of a hydrogenation catalyst, preferably Raney-nickel. The thus hydrogenated, acids then are recrystallized and esterified according to known methods, for example, the Einhorn or Schotten-Baumann reactions, and subjected to multiple recrystallizations until a constant transformation temperature is obtained. The ester products made by this method are the trans-isomers, which can be characterized by the presence of liquid-crystal phases and by their sharp transformation temperatures.

The following examples illustrate the preparation of the novel compounds of the invention.

EXAMPLE 1

7-n-Butyl-Perhydrophenanthren-2-carboxylic Acid 20 g (0.075 mol) of 7-n-butyl-9,10-dihydrophenanthren-2-carboxylic acic acid in 200 ml of 10% aqueous potassium hydroxide is shaken with 30 g of Raney-nickel for 100 hours at a hydrogen pressure of 15 atm. at 260° to 270° C. in an autoclave. Thereafter the catalyst is removed and the crude product is heated with concentrated hydrochloric acid obtain the free acid, which is recrystallized several times from ethanol. The yield is 13.9 g of a white crystalline solid which melts at 160° C. and is nematic up to 219° C.

EXAMPLE 2

7-n-Butyl-Perhydrophenanthren-2-carboxylic Acid Chloride 0.005 mol of 7-n-butyl-perhydrophenanthren-2-carboxylic acid is reacted with 4 to 5 times as much of thionylchloride and a couple of drops of pyridine. After several hours of heating, the excess reagents are distilled off and the acid chloride resultant is used for esterification below according to the method of Einhorn without further purification.

EXAMPLE 3

7-n-Butyl-Perhydrophenanthren-2-carboxylic Acid-4-n-Pentylphenylester 0.005 mol of 4-n-pentylphenol are esterified with an equimolar amount of 7-n-butyl-perhydrophenanthren-2-carboxylic acid chloride in 20 ml of pyridine. The resultant deposit is allowed to stand over night and is subsequently heated for an additional 30 minutes to 70° to 80° C. Following cooling, the reaction product is recrystallized several times from methanol, until its characteristic melting and transition points are reached.

Yield: 50–60%.
K—75, S—114, N—135 I.

EXAMPLE 4

According to the method illustrated in examples 1 to 3 the following compounds are obtained from the corresponding phenolic reactants.

| No. | n | R | N | S | N 1 |
|-----|---|---|---|---|-----|
| 1 | 4 | H | .160 | — | 219 |
| 2 | 4 | —⌬—$C_5H_{11}$ | .75 | .114 | .135 . |
| 3 | 4 | —⌬—$OC_6H_{13}$ | .76 | .136 | .144 . |
| 4 | 4 | —⌬—CN | .79 | — | 185 . |
| 5 | 4 | —⌬—$CH_2CH_2CN$ | .105 | — | 124 . |
| 6 | 4 | —⌬—CH=C(CN)(CN) | .89 | — | 187 . |
| 7 | 4 | —⌬(CH₃)—C(=O)—O—⌬—$OC_4H_9$ | .84 | .114 | .256 . |
| 8 | 4 | —⌬(CH₃)—C(=O)—O—⌬—$OC_8H_{17}$ | .64 | .148 | .108 . |
| 9 | 4 | —⌬—$C_4H_9$ | .86 | — | .114 . |

The following examples illustrate the use of the novel compounds in liquid-crystal compositions

EXAMPLE 5 (STANDARD)

A mixture of 34.5 mol-% of 4-n-propylcyclohexanecarboxylic acid-4-cyanophenylester, 31.0 mol-% of 4-n-butylcyclohexane carboxylic acid-4-cyanophenylester, and 34.5 mol-% of 4-n-pentylcyclohexane carboxylic acid-4-cyanophenylester is used in an opto-electronic cell of the Schadt-Helfrich type (twisted layers). The cell shows following characteristics:

Melting point: 10°–14° C.
Clearing point: 72° C.
Threshold voltage: $U_o$=1.4 V.
Connection time: $t_{E50}$=560 nm.
Disconnection time: $t_{A50}$=240 nm.

EXAMPLE 6

When 20 mol-% of 7-n-butyl-perhydrophenanthren-2-carboxylic acid-4-cyanoethylphenylester is added to the mixture in Example 5, to form a liquid crystal composition, the resultant cell exhibits the following improved characteristics (20° C., layer thickness 10 μm):

Melting temperature: 3°–6° C., can be strongly undercooled for several days.
Clearing temperature: 83° C.
Threshold voltage: $U_o$=1.4 V.
Connection time: $t_{E50}$=370 ms.
Disconnection time: $t_{A50}$=184 ms.

EXAMPLE 7

When 20 mol-% of 7-n-butylperhydrophenanthren-2-carboxylic acid-4-cyanophenylester (compound No. 4 in Example 4) is added to the mixture provided in example 5, the following improved characteristics are noted. (20° C., layer thickness 10 μm):

Melting temperature: The mixture does not crystallize even after having been standing for several weeks in the refrigerator at −10° C.
Clearing temperature: 101°–103° C.
Threshold voltage: $U_o$-2 V.
Connection time: $t_{E50}$=334 ms.
Disconnection time: $^tA50$=126 ms.

We claim:

1. Nematic liquid crystal compounds which are 7-alkyl-perhydrophenathren-2-carboxylic acids and esters thereof having the formula wherein R is

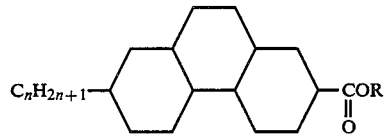

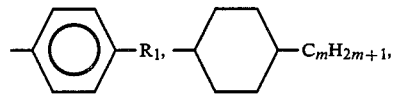

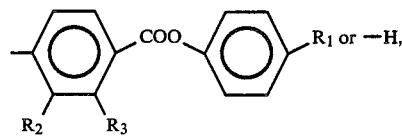

and wherein $R_1$ is —$C_mH_{2m+1}$, —$OC_mH_{2m+1}$, —CH=C(CN)₂, —CN, —$C_2H_4$—CN, —$NO_2$, —F, —Cl, —Br, or —I, and $R_2$ and $R_3$ are individually selected from —H, —$CH_3$, —F, —Cl and —CN, and n and m are 1 to 14.

2. A nematic liquid crystal compound according to claim 1, which is

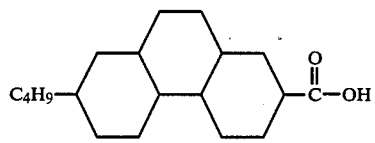

3. A nematic liquid crystal compound according to claim 1, which is

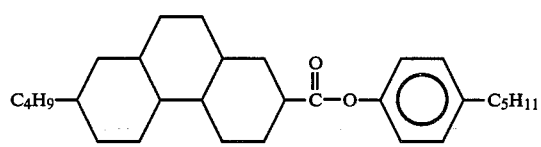

4. A nematic liquid crystal compound according to claim 1, which is

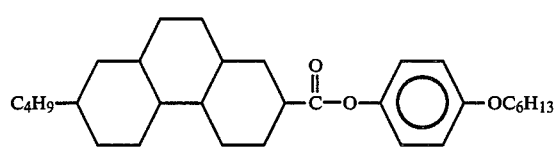

5. A nematic liquid crystal compound according to claim 1, which is

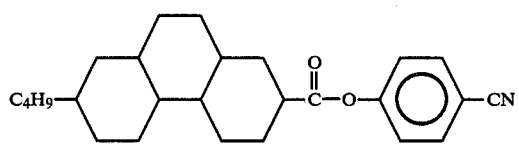

6. A nematic liqud crystal compound according to claim 1, which is

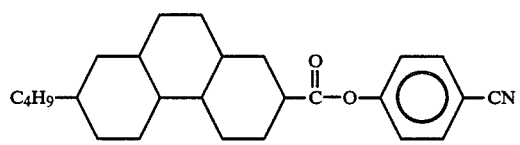

7. A nematic liquid crystal compound according to claim 1, which is

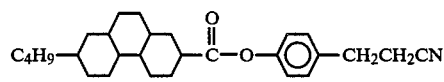

8. A nematic liquid crystal compound according to claim 1, which is

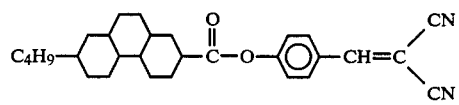

9. A nematic liquid crystal compound according to claim 1, which is

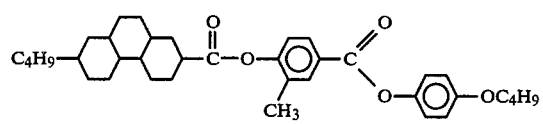

10. A nematic liquid crystal compound according to claim 1, which is

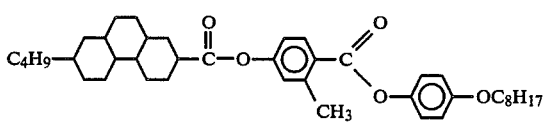

11. A nematic liquid crystal compound according to claim 1, which is

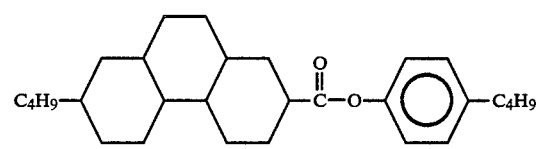

12. A mixture comprising a nematic liquid crystal compound according to claim 1 and the following three compounds in the following proportions relative to each other 34.5 mol-% 4-n-propylcyclohexane carboxylic acid-4-cyanophenylester,
31.0 mol-% 4-n-butylcyclohexane carboxylic acid-4-cyanophenylester, and
34.5 mol-% 4-n-pentylcyclohexane carboxylic acid-4-cyanophenylester.

13. A mixture according to claim 12, consisting of 80 mol-% of said three compounds and the balance 7-n-butylperhydrophenathren-2-carboxylic acid-4-cyanethylphenylester.

14. A mixture according to claim 12, consisting of 80 mol-% of said three compounds and the balance 7-n-butylperhydrophenathren-2-carboxylic acid-4-cyanphenylester.

15. In an opto-electronic display containing at least one nematic liquid crystal compound, the improvement in which the at least one liquid crystal compound comprises a compound according to claim 12.

* * * * *